United States Patent
Wagenknecht

(12) 
(10) Patent No.: US 8,761,482 B2
(45) Date of Patent: Jun. 24, 2014

(54) KNOWLEDGE-BASED SEGMENTATION OF ATTENUATION-RELEVANT REGIONS OF THE HEAD

(75) Inventor: Gudrun Wagenknecht, Stolberg (DE)

(73) Assignee: Forschungszentrum Julich GmbH, Julich (DE)

( * ) Notice: Subject to any disclaimer, the term of this patent is extended or adjusted under 35 U.S.C. 154(b) by 125 days.

(21) Appl. No.: 13/380,291

(22) PCT Filed: Jun. 22, 2010

(86) PCT No.: PCT/EP2010/058811
§ 371 (c)(1),
(2), (4) Date: Mar. 12, 2012

(87) PCT Pub. No.: WO2011/000739
PCT Pub. Date: Jan. 6, 2011

(65) Prior Publication Data
US 2012/0155733 A1    Jun. 21, 2012

(30) Foreign Application Priority Data
Jul. 3, 2009 (DE) .......................... 10 2009 027 448

(51) Int. Cl.
*G06K 9/00* (2006.01)
*A61B 5/05* (2006.01)
(52) U.S. Cl.
USPC ........................................ 382/131; 600/410
(58) Field of Classification Search
USPC ......... 382/128, 129, 130, 131, 132, 133, 134, 382/164, 171; 378/4, 8, 21–27, 101, 901; 600/407, 410, 411, 425, 427; 128/915, 128/916, 920, 922
See application file for complete search history.

(56) References Cited

U.S. PATENT DOCUMENTS

| | | | |
|---|---|---|---|
| 6,430,430 B1 * | 8/2002 | Gosche ...................... | 600/410 |
| 6,567,684 B1 * | 5/2003 | Chenevert et al. ............ | 600/410 |
| 8,295,575 B2 * | 10/2012 | Feldman et al. .............. | 382/131 |
| 2007/0043268 A1 * | 2/2007 | Russell ........................ | 600/300 |

OTHER PUBLICATIONS

International Search report for corresponding application No. PCT/EP2010/058811 completed Feb. 8, 2011.
Wagenknecht G et al: "Wissensbasierte Segemtierung schwaechunsrelevater Regionen des Kopfes in T1-gewichteten MRT-Bilddaten Fuer die Schwaechungskorrektur in MR-Pet Systemen", Nuklearmedizin, Schattauer Verlag, Stuttgart, DE, Bd. 48, Nr. 2, Apr. 22, 2009, Seite V147, XP009136171, ISSN: 0029-5566 das ganze Dokument.
Wagenknecht G et al: "MRI-based Individual 3D region-of-interest atlases of the human brain: a new method for analyzing functional data.", Methods of Information in Medicine 2004 LNKD-PUBMED: 15472751, Bd. 43, Nr. 4, 2004, Seiten 383-390, XP002592300, ISSN: 0026-1270 section 2: Methods.

(Continued)

*Primary Examiner* — Abolfazl Tabatabai
(74) *Attorney, Agent, or Firm* — Renner, Otto, Boisselle & Sklar, LLP

(57) ABSTRACT

The present invention relates to a method and a device for determining attenuation areas in a body. The invention particularly relates to a method and a device for performing magnetic resonance/positron emission tomography measurements utilizing the attenuation areas determined.

31 Claims, 3 Drawing Sheets

(56) References Cited

OTHER PUBLICATIONS

Wagenknecht Gudrun et al: "Individual 3D region-of-interest atlas of the human brain: Knowledge-based class image analysis for extraction of anatomical objects", 2000, Proceedings of SPIE—The International Society for Optical Engineering 200 Society of Photo-Optical Instrumentation Engineers, vols. 3979, p. I/, XP002592301, das ganze Dokument.

Gudrun Wagenknecht et al.: "Knowledge-based segmentation of the head in T1-weighted MR images for attenuation correction in MR/pet systems", 2009 IEEE Nuclear Science Symposium and Medical Imaging Conference (NSS/MIC 2009), IEEE, Orlando, FL, USA, Oct. 24, 2009, Seiten 3338-3343, XP031621139, ISBN: 978-1-4244-3961-4 das ganze Dokument.

Helms G et al.: "Contrast-driven approach to intracranial segmentation using a combination of T2- and T1-weighted 3D MRI data sets", Journal of Magnetic Resonance Imaging Wiley UK, Bd 24, Nr. 4, Oct. 2006, Seiten 790-795, XP002610164, ISSN: 1053-1807 Seite 790-Seite 791 Seite 794.

Zein Salah et al., "Preoperative planning of a complete mastoidectomy: semiautomatic segmentation and evaluation", International Journal of Computer Assisted Radiology and Surgery, vol. 1, No. 4, (Nov. 2006), pp. 213-222.

\* cited by examiner

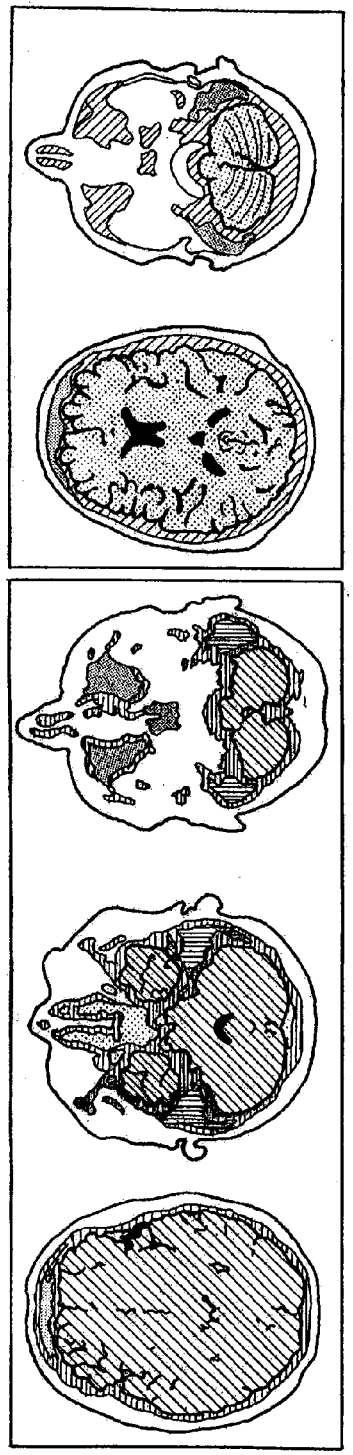

Outline of FIG. 2c

▨ segmented cavities (blue)
▨ further regions (red to yellow)

KNOWLEDGE-BASED SEGMENTATION OF ATTENUATION-RELEVANT REGIONS OF THE HEAD

The present invention relates to a method and a device for determining attenuation areas in a body. The invention particularly relates to a method and a device for performing magnetic resonance/positron emission tomography (MR/PET) measurements utilizing the attenuation areas determined.

Positron emission tomography (abbreviation: PET) is an imaging method in nuclear medicine which generates sectional images of living organisms by making visible the distribution of a weakly radio-labeled substance in the organism and thus mapping biochemical and physiological functions. At the start of an examination, a radiopharmaceutical agent is administered to the living organism, namely radionuclides that emit positrons (beta radiation). During the interaction of a positron with an electron in the body, two high-energy photons are emitted into exactly opposite directions, i.e. at an angle of 180 degrees to one another (annihilation radiation). The PET device comprises detectors for the photons that are disposed annularly around the patient. If two exactly opposite detectors register a photon at the same time, then this event is ascribed to a decay process that has occurred on a straight line between the two detectors. From the distribution of registered decay events in time and space, conclusions are drawn as to the spatial distribution of the radiopharmaceutical agent inside the body and a series of sectional images is computed. PET is frequently used in metabolism-related issues in oncology, neurology and cardiology.

Magnetic resonance tomography (abbreviation MRT) is an imaging method used in medical diagnostics for depicting the structure and function of tissues and organs in the human or animal body. Magnetic resonance tomography is based on very strong magnetic fields and alternating electromagnetic fields in the radio frequency range with which certain atomic nuclei (most frequently hydrogen nuclei/protons) in the body are being excited. What is received are extremely weak electromagnetic fields emitted by the excited atomic nuclei. An essential basis for the image contrast are different relaxation times of different tissue types. In addition, the different hydrogen atom contents in different tissues (e.g. muscle, bone) also contribute to the image contrast.

From the documents "MRI-Based Individual 3D Region-of-Interest Atlases of the Human Brain", G. Wagenknecht, H.-J. Kaiser, U. Buell, O. Sabri, Methods Inf Med 4/2004, pages 383-390; "Individual 3D region-f-interest atlas of the human brain: automatic training point extraction for neural network based classification of brain tissue types", G. Wagenknecht, H.-J. Kaiser, T. Obladen, O. Sabri, U. Buell, SPIE Electronic Imaging 2000, San Jose, Proc SPIE 3962: 150-161; "Individual 3D region-of-interest atlas of the human brain: neural network-based tissue classification with automatic training point extraction", G. Wagenknecht, H.-J. Kaiser, T. Obladen, O. Sabri, U. Buell, SPIE Medical Imaging 2000, San Diego, Proc SPIE 3979: 306-317, it is known to classify the image information obtained by an MR measurement into tissue classes such as gray matter, white matter, liquor (cerebrospinal fluid), adipose tissue and background in order thus to obtain an anatomical image of the examined organism.

A positron emission tomography only permits a measurement of functions, for example in relation to blood flow or metabolism. Structural information cannot be obtained by means of positron emission tomography. In order to additionally obtain structural information, an MR measurement, and thus a morphological measurement, is also carried out. Inter alia, it is thus determined where which tissue regions are to be found, for example, in the case of the brain, so that an association between function and anatomy becomes possible. Thus, the morphology of, for example, a knee joint or of organs can be made visible by means of an MR measurement, which is not possible with positron emission tomography.

As a rule, MRT and PET measurements are today carried out in two different devices, i.e. on the one hand in a magnetic resonance tomograph for carrying out a magnetic resonance tomography, and on the other hand a positron emission tomograph. However, devices also exist—hereinafter referred to as MR/PET devices—(known, for example, from WO 2008/006451 A), which comprise both a magnetic resonance tomograph as well as a positron emission tomograph in order thus to be able to carry out both of the measurements mentioned above without having to move the organism to be examined for this purpose. For if the two measurements are carried out in two different devices, it is practically never possible to position an organism to be examined in the same way such that the image data obtained by both devices relate to the same orientation in space. Thus, attempts must then be made to match (register) the image data sets of an MR measurement to the image data sets of a PET measurement with regard to spatial orientation in order to be able to associate biochemical and/or physiological processes anatomically. Such matching processes are avoided with a device that permits both an MRT as well as a PET examination without having to move an organism for this purpose.

Radiation to be detected within the context of PET or MRT examinations occurs inside the organism and is captured by detectors disposed outside the organism. Because the radiation has to pass areas of the organism such as soft tissues, bones as well as air-filled cavities on the way from its origin to the detector, it is attenuated by these areas (hereinafter also referred to as attenuation regions) and thus incompletely captured by the detectors. The different attenuation regions attenuate radiation to different extents.

The problem with such an attenuation of radiation is that results are distorted thereby if the influence of attenuation is not corrected or not taken into account. In the case of a positron emission tomography, for example, only few decays may be captured, due to attenuation, by the corresponding detectors in the context of a measurement in contrast to reality. In order to determine the true number of decays in such a case and thus obtain correct information, it is necessary to be able to estimate and correct changes due to attenuation. (see R. Standke: Technische Grundlagen der 18F-Fluorodeoxy-glukose-Positronen-emissionstomographie-Diagnostik; Acta Medica Austriaca, Blackwell Verlag, 29th Volume, Issue 5 2002, P. 149-155; also see http://de.wikipedia.org/wiki/Positronen-Emissions-Tomographie#Korrektur_der_Messdaten_(measured attenuation correction with rod-shaped sources); C. Burger, G. Goerres, S. Schoenes, PET attenuation coefficients from CT images: experimental evaluation of the transformation of CT into PET 511 -keV attenuation coefficients. EJNMMI, 29:922-927, 2002. (PET-CT: calculated attenuation correction); M. Hofmann, et al, MRI-Based Attenuation Correction for PET/MRI: A Novel Approach Combining Pattern Recognition and Atlas registration. JNM, 49:1875-1883, 2008. (MR/PET: calculated attenuation correction); Tyler D J, Robson M D, Henkelman R M, Young I R, and Bydder G M Magnetic Resonance Imaging with Ultrashort TE (UTE) Pulse Sequences: Technical Considerations J Magn Reson Imaging (2007) 25:279-289 (the aim is the development of novel sequences that permit an improved differentiation of bone tissue)).

In order to be able to correct the attenuation of a detected radiation, it is necessary to know which attenuation regions the radiation had to pass through in order to arrive at the respective detector. The image data required therefor that supply the anatomical information necessary for this can originate, as was already mentioned, from an MRT measurement. However, not all interesting attenuation regions or attenuation areas can be differentiated based on the intensity values (gray values) by means of these image data. For example, it is not possible to distinguish between bone areas and air-filled cavities because they are depicted in the same gray value range. However, that would be necessary in order to correctly determine whether radiation was attenuated by a bone or whether it has passed through an air-filled cavity.

It is an object of the present invention to determine attenuation areas in an improved manner in order to be able to further develop MR/PET technology.

In order to achieve the object, an animal or human body is captured entirely or partially by means of magnetic resonance tomography so that an MRT image data set is obtained. The gray values of the MRT image data set are classified in such a way that each gray value is assigned to a tissue class. For the above mentioned reasons, such a first assignment is possible only as an approximation because not all attenuation areas can be uniquely identified based on the gray values. Therefore, the voxels of the image data set classified based on the gray values are subsequently compared with the anatomy of the examined body or examined body part in order to check whether the result of the classification is plausible. If the comparison yields the result that the result of the gray-value based classification of a voxel cannot match the anatomy of the examined body or examined body part, the voxel is reclassified in such a way that there is no discrepancy anymore between the assignment to a tissue class and the known anatomy. Therefore, a reclassification occurs in accordance with the comparison made.

Attenuation areas in a body can thus be determined in an improved manner. The knowledge about the position and extent of the attenuation areas in the examined body or examined body part thus improved makes it possible to determine and correct the attenuation of radiation in an improved manner.

If multi-spectral MRT image data were to be used, i.e. several sequences, several parameters (gray values) per voxel would be obtained (i.e. a vector) with which classification would be carried out. The invention could be used accordingly in such cases.

FIG. 2a shows images illustrating results from a data set in which differently attenuating areas of the head are segmented.

FIG. 2b shows additional images illustrating results from the data set in which differently attenuating areas of the head are segmented.

Figure 1:
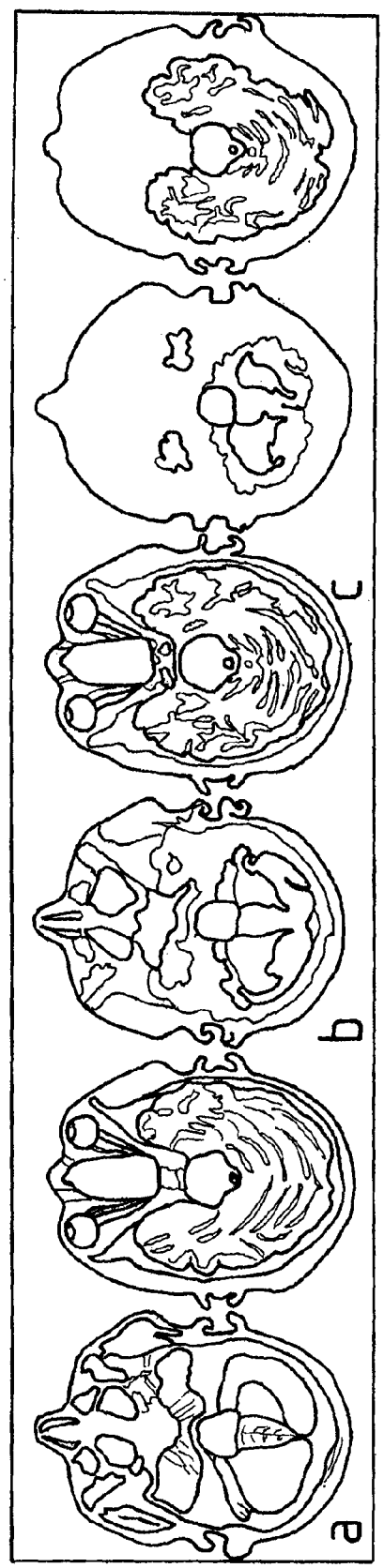
FIG. 1 shows images illustrating results from a data set in which the cerebral region is divided into different brain tissue classes.

In one embodiment of the invention, a body of a living organism is examined entirely or partially by means of positron emission tomography and a PET image data set is thus obtained. Moreover, the living organism is examined entirely or partially by means of magnetic resonance tomography and an MRT image data set is obtained. If a living organism is examined only partially, then the PET and MRT examinations relate to the same area, for example, the head of the living organism. Preferably, both measurements are carried out in a MR/PET device. Otherwise, the two image data sets are to be matched (registered) to one another in such a way that the two image data sets relate to the same spatial orientation.

The PET image data serve for showing the function in an organ (as was already mentioned above), and these PET image data are attenuation-corrected. If this were not done, the measured function (e.g. metabolism or blood flow) would not be determined correctly, which in turn affects diagnostics (e.g. metabolism too low due to attenuation ->underestimation ->in the worst case: false diagnosis). With the present invention, the decisive attenuation regions are determined in an improved manner from the MRT image data. Thus, PET image data can be corrected accordingly in an improved manner.

An MRT image data set thus obtained comprises a plurality of voxels, to each of which is assigned a gray value. The gray values are now classified as described, that is, each examined gray value is interpreted as belonging to a certain area (hereinafter referred to as "tissue class") and assigned accordingly. For example, if a head is examined, then the gray values of an MRT image data set are interpreted as gray matter, white matter, liquor (cerebrospinal fluid), adipose tissue and background and assigned accordingly. T1-weighted measurement results generated based on 3D sequences are preferably used for carrying out the classification because they have a particularly high resolution, show the essential tissue types with high contrast and have a good signal-to-noise ratio at a measuring time acceptable to the patient. Therefore, these data are ideally suited for the segmentation of anatomical structures. If such a high accuracy is not required, alternative MR sequences or combinations or image data originating from different sequences can also be used. What is important in this respect is that the areas to be segmented are being shown with high contrast.

In one embodiment of the invention, in order to carry out the classification, an area or section of the examined living organism is first examined and analyzed which comprises all tissue classes. In the case of the head, a section through the head is thus examined which is known to comprise the tissue classes gray matter, white matter, liquor (cerebrospinal fluid), adipose tissue and background. A central transaxial section through a human brain, for example, is suitable therefor. The five above-mentioned tissue classes, whose anatomy, and thus properties, such as homogeneity, size and spatial position relative to one another is known, can be found in this sectional plane. At first limited to this area, the gray values of the voxels belonging to this section are classified approximately. Thus, it is determined, based on the known anatomy, which gray value is to be assigned to which tissue class. If the classification process has been trained sufficiently in this manner, then the other voxels of the MRT image data set, based on this assignment, are classified based on their gray values.

As a result of the tissue classification, a data set 1 of a class image is obtained in which every voxel is assigned to a tissue class, that is, in the case of the head to one of the classes gray matter (GM), white matter (WM), cerebrospinal fluid (CSF), adipose tissue (AT) and background (BG).

In one embodiment of the invention, all voxels are examined which have been classified as background (BG), and it is determined whether a voxel classified as background actually lies outside the examined body or body area. If this examination shows that a voxel lies within the examined body and was nevertheless classified as background due to its gray value, then it is suitably reclassified, namely in accordance with the anatomy of the examined body or examined body part. Reclassification is carried out in such a way that the classification into another tissue class does not contradict the known anatomy of the examined body or examined body area.

If a voxel has been classified as background (BG), then it is supposed to be an area lying outside the body. In one embodiment of the invention, all voxels are determined which lie outside the examined, known body or examined, known body area. If there are voxels amongst them that have not been classified as background due to their gray value, then they are reclassified or relabeled and are thus assigned to the class BG.
Step 1:

In one embodiment of the invention, in the case of an examination of a head, the area of the tissue class BG lying outside the head is first captured in every layer of the data set, for example by 2D region growing. The remaining BG voxels, which, for example, have not been captured in the region growing, thus lie inside the head and are relabeled into CSF because they cannot be background. Then, the area of the head is captured, for example, with 3D region growing. All voxels that do not belong to the head are then assigned to the tissue class BG. False classifications in the area of the background which can be caused, for example, by noise or motion artifacts during the measurement of the patient, are thus eliminated.

Region growing is an image segmenting method. In this method, homogenous image elements are merged into regions. First, the image is divided into initial cells ($1 \times 1 \times 1$, $2 \times 2 \times 2$ or $4 \times 4 \times 4$ voxels). Starting with the selection of an initial cell as a starting region, this is then compared with the adjacent cells, wherein, for example, the average values of the gray values of the region and of the adjacent cell can be examined. If they are similar, they are merged. In the present invention, the class affiliation of the voxels is considered, and merging is carried out if the desired class affiliation is provided. The region continues to grow by comparison with all its neighbors. If no neighbors can be added anymore, a region has been found, and a new cell is selected which does not yet belong to a region and the process is started again at the beginning. The whole process is repeated until all pixels or voxels have been assigned to regions.
Step 2:

In one preferred embodiment, in order to separate the extracerebral region from the cerebral region, the two eye regions of the head are first detected and segmented because there is a pronounced connection between the two regions due to the optical nerve. These regions lie laterally/anteriorly in the central layer area of the head and are surrounded by adipose tissue due to the corpus adiposum orbitae. Therefore, detection takes place by means of an appropriately sized and shaped, preferably square, transaxial template of the tissue class AT. A template is a reference object (in this case of a certain shape and class property) which is moved over an area of the image. At every position of the template, all voxels of the image that are scanned by the template are compared with the respective voxel of the template (in this case the class property). (The basic principle is known and is apparent from the web site http://en.wikipedia.org/wiki/Template_matching (as of 18 Jun. 2009). In our case, however, the template is not an image section with a complex image content, but with a particular class property.) "Appropriately sized" in this context refers to the approximate size to be expected and a (very) rough shape of an anatomical region.

The image data are present in a three-dimensional matrix in which each voxel of the matrix has a class label. In the central/front area of the three-dimensional image matrix, the template is moved, starting from the front, on the left and right side (in anatomical terms: lateral) until the region of the class AT in which the greatest number of voxels of the AT template is superposed with voxels of the AT region has respectively been found independently from one another on both sides. All voxels of the class AT superposed by the template on the right and left side are given the class label "EYE". Then, the area of the adipose tissue is captured completely by 3D region growing and labeled as EYE. Then, this area is dilated into the area WM, and then in the area GM, in order thus to capture the eye region including the optical nerves.

Dilating means that the area is expanded at the edges (also see http://de.wikipedia.org/wiki/Dilatation (Bildverarbeituna), as of 18 Jun. 2009). For this purpose, a structural element is selected and compared to this (e.g. an element of the size $3 \times 3 \times 3$). The process of dilation can be repeated iteratively.
Step 3:

Subsequent thereto, the brain region is next separated from the extracerebral area by erosion in one embodiment of the method. Just like dilation, erosion is a basic operation of morphological image processing. Erosion is realized by means of a structural element (e.g. an element of the size $3 \times 3 \times 3$). For each structural element, a reference point is defined which permits placing the element at a particular voxel position. The actual operation consists of the voxel-by-voxel displacement of the structural element over the total image. A check is carried out whether the structured element fits into the set completely.

Since the brain is surrounded by cerebrospinal fluid, the area CSF is now dilated by erosion. For this purpose, the voxels of the classes GM, WM and AT are eroded in the neighborhood of CSF and assigned to CSF. CSF is thus indirectly dilated.

Since the brain is surrounded by cerebrospinal fluid, the area CSF is now dilated by erosion. For this purpose, the voxels of the classes GM, WM and AT are eroded in the vicinity of CSF and assigned to CSF. CSF is thus indirectly dilated.

In one embodiment, this area is captured by a subsequent 3D region growing, and all other voxels of the class GM, WM and AT (which lie in the extracerebral area) are relabeled into CSF. The extracerebral area is now assigned completely to CSF. Within the brain region, all voxels of the class AT are assigned to the class WM because they are incorrectly classified adipose-tissue voxels that cannot occur within the brain. Because the gray values of the adipose tissue in the original MRT image data set are similar to those of the white matter, AT voxels are relabeled into WM.
Step 4:

Since the brain region was made smaller by erosion for the purpose of separating the extracerebral area, this is now reversed in one embodiment of the invention by dilation operations. Since the white matter of the brain (WM) is surrounded by a thin cortex of the gray matter (GM), but because this GM area has possibly been eroded completely in some places by the erosion, the area of the class WM is first dilated into the area CSF. In addition, voxels that prior to the erosion belonged to the class AT are reassigned to the class WM in this dilation. Then, the cortex is reconstructed by the area of the class GM being dilated into the area CSF. Finally, all voxels of the region EYE are also assigned to CSF. The brain is now reconstructed again and the extracerebral area is completely assigned to the class CSF.
Step 5:

In one embodiment of the invention, the area CSF in the extracerebral region is now reduced. For this purpose, the class SB is dilated in each transaxial layer from the border area of the head in the direction of the brain, starting from the CSF voxels neighboring the background outside the head (BG). To this end, CSF voxels that, in the same layer, are surrounded exclusively by adjacent voxels of the classes BG, CSF or SB, are converted into the class SB. Then, the neighborhood is examined in 3D. SB voxels in the neighborhood of GM or WM are converted into CSF voxels because cerebrospinal fluid has to be around the brain. The extracerebral area is now assigned to SB and the cerebral area is assigned to the classes GM, WM and CSF.

Step 6:

Problems may occur in the area of the auditory canals because this area of the auditory canals classified as BG can additionally be connected to the area of the background which actually lies outside of the head. On the other side, the auditory canals are in the neighborhood of the mastoid cell regions and can be connected to these extensive regions which are also classified as BG. This leads to a large area within the head being erroneously considered as lying outside of the head (since it belongs to BG). In one embodiment, because the auditory canal has, in the vicinity of the actual background, a rather small size, this area is first closed by the class SB being dilated into the area BG. Thus, the border areas of the head are naturally also dilated into the background. By subsequent 3D region growing in the area of the class BG outside of the head, the background can be captured. The area of the BG voxels and dilated SB voxels not captured by region growing is now relabeled into TEMP. The enlargement of the head area is reversed by the area BG being dilated into the area TEMP. The remaining TEMP voxels are then relabeled into SB and the extracerebral area is fully segmented.

It was found that particularly good results are obtained if the above sequence of steps is adhered to. If the above sequence is only partially adhered to, then the result obtained is not optimal, but nevertheless an improved result as compared with the prior art.

The result obtained is a data set in which the cerebral region is divided into the different brain tissue classes (class image in which each voxel of the cerebral area is assigned to one of the classes gray matter (GM), white matter (WM) and cerebrospinal fluid (CSF), and in which each voxel of the extracerebral area of the head is assigned to the class scalp/bone (SB), and each voxel not belonging to the head is assigned to the class background (BG). FIG. 1 illustrates the results. The two images a show slices of a T1-weighted input image data set. The two images b show the result of the tissue classification obtained therefrom. The two images c show the results of the cerebral and extracerebral separation obtained therefrom.

The following is based on an obtained first data set 1 relating to a human head, which resulted from a tissue classification. Data set 1 is a tissue class image in which every voxel is assigned to one of the tissue classes gray matter (GM), white matter (WM), cerebrospinal fluid (CSF), adipose tissue (AT) and background (BG). Moreover, a second data set 2, which resulted from a separation of the cerebral and extracerebral region, is taken as a basis. Data set 2 is a class image in which each voxel of the brain is assigned to one of the classes gray matter (GM), white matter (WM) and cerebrospinal fluid (CSF), and in which each voxel of the extracerebral area of the head is assigned to the class (SB), and each voxel not belonging to the head is assigned to the class background.

The extracerebral area of the head is subsequently segmented, so that each voxel of this area is assigned to one of the cavity areas (classes MASTOID, SINUS1-SINUS4), the bone (class BONE) or to the extracerebral soft tissues (class SOFT):

Region in the temporal bone [lat. os temporale]:
Mastoid cell region [lat. processus mastoideus] (class: MASTOID);
Cavities in the Viscerocranium:
frontal sinus [lat. sinus frontalis] (class: SINUS1), the region of the nasal
cavity [lat. cavum nasi], ethmoid cells [lat. cellulae ethmoidales] and
sphenoid sinus [lat. sinus sphenoidalis] (class: SiNUS2), maxillary sinus [lat. sinus maxillaris] (class: SINUS3) and pharynx [lat. pharynx] (class: SINUS4);
Bone Regions:
Bones of the cranium [lat. neurocranium] and of the viscerocranium [lat. viscerocranium] (class: BONE)
Soft tissue region: soft tissue of the extracerebral region of the head, e.g. muscles, adipose tissue, skin etc. (class: SOFT)
The process preferably is as follows:
First, the region of the brain (cerebrum and cerebellum, brain stem) is processed as follows: Based on data set 2, all voxels of the classes WM and GM are assigned to the class WMGM because the attenuation properties of these areas are considered the same. All voxels of the class CSF are first retained because they are important for the reconstruction of the areas of the cranial bones. Finally, however, the voxels of the class WMGM and CSF can be assigned to a unified class BRAIN which then receives an attenuation value.

The extracerebral region of the head is given by all the voxels of the class SB in the data set 2. In this area, the class affiliation of all voxels in the data set 1 is examined. Cavity regions and bone regions substantially have in data set 1 the class affiliation BG or CSF, the extracerebral soft tissue regions substantially have the class affiliation GM, WM or AT, which are now combined into a single class SOFT. Using these class affiliations, the process for segmenting the extracerebral region into attenuation-relevant areas is as follows:

First, the two mastoid cell regions (MASTOID) are detected and segmented. Then, the cavities in the viscerocranium are detected and segmented in the order frontal sinus (SINUS1), nasal cavity, ethmoid cells and sphenoid sinus (SINUS2), maxillary sinuses (SINUS3) and pharynx (SINUS4). In the process, the anatomical knowledge about the positional relationships of these regions is taken into account in the detection. In this case, segmentation means the assignment of each voxel of this region to the corresponding class. The class property of the voxels in data set 1 which belong either to class CSF or BG is taken into account during segmentation.

Then, the area of the bones (BONE) is reconstructed. In the process, the knowledge about the positional relationships of the bone regions to the brain region (see above, CSF surrounds the brain (cerebrum and cerebellum, brain stem) in data set 2) and to the cavities already detected (mastoid cell regions, cavities in the viscerocranium) is taken into account for detection. In this case, segmentation means the assignment of each voxel of this region to the corresponding class. The class property of the voxels in data set 1 which belong either to class CSF or BG and the connection of all cranial and viscerocranial bones is taken into account during segmentation.

Finally, all remaining voxels that are not assigned to any of the classes MASTOID, SINUS1-4 or BONE OR SOFT and at the same time belong to the extracerebral area in data set 2 are assigned to the class SOFT. Alternatively, the classes SINUS1-4 can at the end be combined into one class SINUS. Also, the class CSF and GMWM can be merged into a class BRAIN.

The individual steps of detection and segmentation will now be described in more detail for the regions to be extracted in the order of their extraction:

Step 1:

The areas of the class BG (data set 1) located in the extracerebral area (data set 2) are dilated into the area of the class CSF (data set 1), provided that the CSF voxels are located in the extracerebral area (data set 2), because the BG regions belong to cavities or bones in any case, and the CSF areas around the BG areas also belong to cavities or bones due to partial volume effects. In contrast, CSF voxels that are not in the neighborhood of BG areas rather do not belong to cavities or bones and are therefore now assigned (at first) to the class SOFT. Then, the area BG is eroded again in order to separate the interconnected regions. For this purpose, the border area produced by erosion is at first assigned to a temporary class TEMP.

Step 2:

Now, the two mastoid cell regions are detected and segmented as the first regions. These regions are located in the head, laterally/posteriorly of the auditory canal. Therefore, detection is carried out by means of a transaxial template of the class BG that has a suitable size and shape (in this case a square shape) for the anatomical region. This template is displaced in the lower/rear area of the matrix (in anatomical terms: caudal/posterior), starting from the rear, on the left and right side (in anatomical terms: lateral) until the region of the class BG in which the greatest number of voxels of the BG template is superposed with voxels of the BG region has respectively been found independently from one another on both sides. All voxels of the class BG (data set 1) superposed by the template on the right and left side are given the class label MASTOID. The area MASTOID is then dilated into the area BG by dilation in order to capture the entire mastoid cell region.

Step 3:

As the next region, the frontal sinus region is detected and segmented. This region lies median/cranially/anteriorly in the head. Therefore, detection is carried out by means of a transaxial template of the class BG that has a suitable size and shape (in this case rectangular, narrow and long in the lateral direction) for the anatomical region. This template is displaced in the upper/front area of the matrix (in anatomical terms: cranial/anterior), starting from the front, between the template positions of the MASTOID template (i.e. in the median area) until the region of the class BG in which the greatest number of voxels of the BG template is superposed with voxels of the BG region has been found. All voxels of the class BG (data set 1) superposed by the template are given the class label SINUS1. The area SINUS1 is then dilated into the area BG by dilation in order to capture the entire sinus frontalis region.

Step 4:

As the next region, the region of the nasal cavity, ethmoid cells and sphenoid sinus is detected and segmented. This region is given a single class label SINUS 2 because the transitions are so large that a separation is hardly possible. This region lies median/anteriorly and caudally (below) of the sinus frontalis region. Therefore, detection is carried out by means of a transaxial template of the class BG that has a suitable size and shape (in this case rectangular, narrow and long in the anterior-posterior direction) for the anatomical region. Starting from the template position of the SINUS 1 template in the central/front area of the matrix, this template is displaced, starting from the front/top (anterior/cranial), until the region of the class BG in which the greatest number of voxels of the BG template is superposed with voxels of the BG region has been found. All voxels of the class BG (data set 1) and SINUS1 superposed by the template are given the class label SINUS2. The area SINUS2 is then dilated into the area BG and SINUS1 by dilation (first transaxially 2D and then 3D) in order to capture the entire area of the nasal cavity, ethmoid cells and sphenoid sinus.

Step 5:

Now, the two maxillary sinuses are detected and segmented as the next regions. These regions are located median/anteriorly in the head and caudally (below) of the region of the nasal cavity, ethmoid cells and sphenoid sinus. Therefore, detection is carried out by means of a transaxial template of the class BG that has a suitable size and shape (in this case almost square, slightly longer in the anterior-posterior direction) for the anatomical region. Starting from the template position of the SINUS 2 template in the central/front area of the matrix, this template is displaced, starting from the front/top (anterior/cranial), on the left and the right side until the region of the class BG in which the greatest number of voxels of the BG template is superposed with voxels of the BG region has respectively been found independently from one another on both sides. All voxels of the class BG (data set 1) and SINUS2 superposed by the template on the right and left side are given the class label SINUS3. The area SINUS3 is then dilated into the area BG and SINUS2 by dilation (first transaxially 2D and then 3D) in order to capture the entire area of the maxillary sinuses.

Step 6:

As the next region, the pharynx region is detected and segmented. This region is located median/anteriorly in the head and caudally (below) of the region of the nasal cavity, ethmoid cells and sphenoid sinus and behind the area of the maxillary sinuses. Therefore, detection is carried out by means of a transaxial template of the class BG that has a suitable size and shape (in this case square) for the anatomical region. Starting from the template position of the SINUS 2 template behind (posterior) the central position of the SINUS3 template in the lower/front area of the matrix, this template is displaced, starting from the front/top (anterior/cranial), until the region of the class BG in which the greatest number of voxels of the BG template is superposed with voxels of the BG region has been found. All voxels of the class BG (data set 1) superposed by the template are given the class label SINUS4. The area SINUS4 is then dilated into the area BG and SINUS3 by dilation in order to capture the entire area of the pharynx.

Step 7:

Since dilations were employed, it is not yet ensured that the entire area of the cavities located in the viscerocranium has been captured completely. Therefore, possible gaps between the regions are now closed. These are the areas of the class BG (data set 1) between the regions SINUS1-SINUS4 that have not yet been given a label. This takes place by dilation of the central regions, first SINUS2, then SINUS3, into the area BG. The area SINUS4 is then expanded downwards (caudally) into the area BG (data set 1) by dilation. Then, the area SINUS4 is dilated into TEMP within the transaxial orientation, because the pharynx is not surrounded by viscerocranial bones (see below).

Step 8:

Because all cavity areas have now been labeled completely, the extracerebral BG voxels that still remain are first relabeled into TEMP in order to prepare the bone reconstruction. TEMP voxels of the extracerebral area which are located in the border areas of the background BG (data set 2) surrounding the head are relabeled into SOFT, because the bones are located within the head and are surrounded by soft tissue (SOFT).

Step 9:

Now the bone reconstruction is carried out, starting from the mastoid cell region and the frontal sinus region. The TEMP voxels in the neighborhood of MASTOID and SINUS1 voxels are relabeled into BONE. They serve as seed voxels for subsequent region growing into the area TEMP. The fact that the cranial and viscerocranial bones are connected is exploited in this case. All TEMP voxels not captured by region growing are now relabeled into SOFT because they obviously do not belong to the bone area. The areas of the class BONE surrounding the regions SINUS2-SINUS4 are now supposed to be excluded from the further bone reconstruction, because the bone is not very thick here, and is therefore not supposed to be expanded. To this end, the region SINUS2 is dilated caudally and SINUS3-SINUS4 is dilated into the area BONE, and the dilated area is then relabeled into TEMP.

Step 10:

Now, the reconstruction of the bone takes place additionally, starting from the area CSF (data set 1) surrounding the brain tissue (cerebrum, cerebellum, brain stem), because the brain "swims" in the cerebrospinal fluid, and that is surrounded by bone. For this purpose, the CSF region (data set 2) is dilated into the area SOFT if the examined extracerebral voxel in data set 1 belongs to the class BG or CSF. This extracerebral CSF area is relabeled into TEMP1 and serves as a starting point for the expansion of the cranial bone area. For this purpose, the area TEMP 1 is dilated into the area BONE.

In addition, errors are corrected that may arise due to partial volume effects, for example. These errors lead to areas being present around the cerebrospinal fluid of the brain that are classified as WM, GM or AT (data set 1). In order also to take these areas into account for bone reconstruction, the CSF region of the brain (data set 2) is at first dilated into the area SOFT at such places, and the dilated voxels are relabeled into TEMP1. The TEMP1 area is then further dilated into the area SOFT if the examined extracerebral voxel in data set 1 belongs to the class BG or CSF.

Thus, the reconstruction of the bone is completed. At the end, all TEMP and TEMP1 voxels are relabeled into BONE.

As a result, a data set is obtained in which the differently attenuating areas of the head are segmented. The data set is a class image or tissue class image in which each voxel of a cerebral area is assigned to one of the classes brain tissue (GMWM) and cerebrospinal fluid (CSF), and in which each voxel of the extracerebral area of the head is assigned to one of the classes mastoid cell region (MASTOID), cavities in the viscerocranium (SINUS1-SINUS4), bone (BONE) and soft tissue (SOFT). A result thus obtained is shown in FIGS. 2a-2c.

Figure 2C:
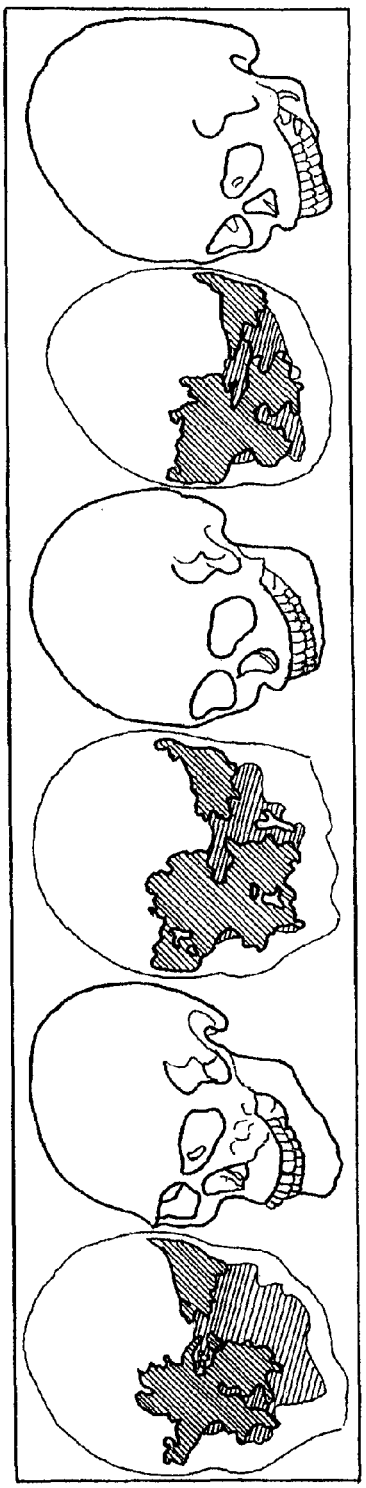
FIG. 2c shows further images illustrating results from the data set in which differently attenuating areas of the head are segmented.

The three illustrations in FIG. 2a show sections through class images by way of example. In this case, all cerebral voxels of the class GMWM are shown in green, the voxels of the class CSF in dark green. In the extracerebral area, all voxels of the class SOFT are shown in white, the voxels of the class BONE flesh-colored. The voxels of the class MASTOID are shown in violet, the frontal sinus voxels (class SINUS1) pink, the voxels of the class SINUS2 red, the voxels of the maxillary sinus (class SINUS3) orange and the voxels of the class SINUS4 yellow. The two illustrations in FIG. 2b show by way of example sections through class images, superposed in color on the gray-scale original slices of the underlying T1-weighted input image data, in order to illustrate the quality of the segmentation results. The background (class BG) is respectively shown in black in the illustrations in FIGS. 2a and 2b. The six illustrations in FIGS. 2c show 3D illustrations of three segmented heads. Two illustrations per head are shown. The left illustration, respectively, shows the surface of all segmented cavities in blue. For spatial allocation of the cavity regions in the head, the other areas are shown in the colors red to yellow and, in addition, transparent. The right illustration, respectively, shows the surface of the segmented cranial bones in blue. Both the 2D as well as the 3D illustrations show by way of example the very good quality of the results for different input image data.

Alternatively, the areas CSF and GMWM can be combined into a single class (BRAIN), because the attenuation properties hardly differ. The same applies for the cavities in the viscerocranium (SINUS1-SINUS4). They can be combined into a region SINUS. Because the mastoid cell region consists of air and bone portions, this region has to be examined separately.

It was found that particularly good results are obtained if the above sequence of steps is adhered to. If the above sequence is only partially adhered to, then the result obtained is not optimal, but nevertheless an improved result as compared with the prior art.

The MR/PET used preferably according to the invention is a device for carrying out diagnostic examinations. A technological realization of an MR/PET tomography system is comprised of, for example, a 3 Tesla MRT device into which a so-called PET insert has been inserted (for example, the commercially available Siemens 3T MR/PET TimTrio system). Computer systems are used for controlling the device, for image data reconstruction and for diagnostic evaluation of the image data. A standard PC was used to carry out the method according to the invention.

The computing time on a PC Pentium IV, 3.4 GHz, 2 GB main memory is 0.5 sec for the sample extraction for training the classification method, 12.6 sec for the classification of a 256 3D matrix, 2 min 47.5 sec for the separation of the cerebral and extracerebral region, 36.1 sec for the segmentation of the extracerebral region into cavities, bones and soft tissue.

In this method, no additional CT or PET transmission measurement is required, and thus no additional radiation exposure. No non-linear registrations are required which are necessary when using atlases, for example CT-based atlases.

In the method presented above, MRT-based morphological imaging is used for PET attenuation correction by determining the areas that attenuate in varying degrees from the morphological image data. By assigning suitable attenuation coefficients for 511 keV radiation to each voxel of the differently attenuating areas ("Alternative methods for attenuation correction for PET images in MR-PET scanners", E. Rota Kops, H. Herzog, IEEE NSS/MIC Conf Record 2007, pp. 4327-4330, "Magnetic resonance imaging guided attenuation and scatter corrections in three-dimensional brain positron emission tomography", H. Zaidi, M. L. Montandon, D. O. Slosman, Med. Phys., vol. 30, pp. 937-948, 2003.) the segmented image data are converted into attenuation maps. Currently, the following values are used for the segmented attenuation areas of the head: 0.098 1/cm for BRAIN, 0.146 1/cm for BONE, 0.096 1/cm for SOFT, 0.054 1/cm for MASTOID and 0.0 1/cm for SINUS1-4 ("Attenuation Correction in MR-PET Scanners with Segmented T1-weighted MR images", E. Rota Kops, G. Wagenknecht et al., submitted to IEEE MIC 2009). With regard to the attenuation correction of the PET image data, the procedure may be as follows. The attenuation map image data are registered with the PET image data, smoothed and adapted to the matrix and voxel size of the PET image data. They are converted by forward projection into attenuation correction factors (ACF), which are used in the reconstruction of the PET emission image data for attenuation correction.

The invention claimed is:

1. Method for the determination of attenuation areas in an organism, comprising the steps of:
an animal or human body is captured entirely or partially by means of magnetic resonance tomography so that an MR image data set is obtained;
the gray values of the MR image data set are classified in such a way that the gray values are assigned to tissue classes,
the voxels classified based on the gray values are compared with the anatomy of the body and reclassified in accordance with the result;
wherein, for a head, a first data set is obtained from a tissue classification and a second data set is obtained by separating the cerebral and the extracerebral region, and the extracerebral area of the head is subsequently segmented based on the two data sets, so that each voxel of this area is assigned to one of the cavity areas (classes MASTOID, SINUS1-SINUS4), the bone (class BONE) or to the extracerebral soft tissues (class SOFT).

2. Method according to claim 1, according to which the head is captured by means of magnetic resonance tomography so that an MR image data set is obtained and the gray values of the MR image data set are interpreted as gray matter, white matter, liquor (cerebrospinal fluid), adipose tissue and background and assigned accordingly.

3. Method according to claim 1, wherein the animal or human body is captured entirely or partially by means of positron emission tomography, preferably in an MR/PET device.

4. Method according to claim 1, wherein those voxels are determined which lie within the body and have been classified as background (BG), and these voxels are reclassified in accordance with the known anatomy of the body.

5. Method according to claim 1, wherein those voxels are determined which lie outside the body, and each of these voxels is assigned to the class background (BG), even those voxels which had before been classified differently due to their gray value.

6. Method according to claim 1, wherein, for separating the extracerebral region from the cerebral region of the head, the two eye regions are segmented before other regions of the head are segmented.

7. Method according to claim 1, wherein, subsequent to a segmentation of eye regions, a brain region is separated by erosion and captured by region growing.

8. Method according to claim 7, wherein subsequent to the erosion, the brain is reconstructed by dilation.

9. Method according to claim 1, wherein, subsequent to a reconstruction of a brain, the area of the cerebrospinal fluid surrounding the brain is reconstructed and the extracerebral area is assigned to a class.

10. Method according to claim 1, wherein, subsequently, those regions are segmented separately which are connected to the background outside of the head through the auditory canals.

11. Method according to claim 1, wherein voxels of the classes white matter and gray matter are assigned to a unified class (WMGM) based on the second data set.

12. Method according to claim 1, wherein voxels of the classes white matter, gray matter and adipose tissue are assigned to a unified class (SOFT) based on the first data set if these voxels, in the second data set, belong to the extracerebral area of the head.

13. Method according to claim 1, wherein areas (BG) located in the extracerebral area are dilated into the area of cerebrospinal fluid (CSF) if the cerebrospinal-fluid voxels are located in the extracerebral area.

14. Method according to claim 13, wherein voxels of the joint class (WMGM) and voxels of the class cerebrospinal fluid are assigned to a unified class (BRAIN).

15. Method according to claim 1, wherein areas (BG) located in the extracerebral area are eroded in order to separate interconnected regions.

16. Method according to claim 1, wherein the two mastoid cell regions and then the areas of the cavities located in the viscerocranium are detected and segmented, taking into account the positional relationships of the anatomical regions relative to one another.

17. Method according to claim 16, wherein the detection and segmentation is carried out by means of template matching and subsequent dilation.

18. Method according to claim 1, wherein two mastoid cell regions are detected and segmented.

19. Method according to claim 18, wherein the region of the frontal sinus is subsequently detected and segmented.

20. Method according to claim 19, wherein the region of the nasal cavity, ethmoid cells and sphenoid sinus is subsequently detected and segmented.

21. Method according to claim 20, wherein the two maxillary sinuses are subsequently detected and segmented.

22. Method according to claim 21, wherein the region of the pharynx is subsequently detected and segmented.

23. Method according to claim 1, wherein all voxels that in data set 2 belong to the extracerebral area and in data set 1 belong to a class background (BG), and which have not yet been assigned to any of the classes MASTOID, SINUS1-4, are reclassified for preparing the bone reconstruction.

24. Method according to claim 23, wherein bones are subsequently detected and reconstructed, taking into account the positional relationships of the bones to the brain region and to the cavities, as well as taking into account the connection of the bones.

25. Method according to claim 24, wherein the bone reconstruction takes place starting first from the mastoid cell regions and the frontal sinus region, and then from the region of the cerebrospinal fluid surrounding the brain.

26. Method according to claim 23, wherein a detection and segmentation of the bones is carried out by means of reclassification, region growing and dilation.

27. Method according to claim 1, wherein all voxels that belong to the extracerebral area in data set 2 and which are not assigned to any of the classes MASTOID, SINUS1-4 or BONE are assigned to the soft tissues SOFT.

28. Method according to claim 1, wherein voxels of the classes (SINUS1-SINUS4) are assigned to a unified class (SINUS).

29. Method according to claim 1, wherein a finally assigned class is given an attenuation value corresponding to the class.

30. Method according to claim 1, wherein gaps between the cavity areas are closed by dilation and the area is expanded by dilation.

31. Method for the determination of attenuation areas in an organism, comprising the steps of:
an animal or human body is captured entirely or partially by means of magnetic resonance tomography so that an MR image data set is obtained;

the gray values of the MR image data set are classified in such a way that the gray values are assigned to tissue classes, the voxels classified based on the gray values are compared with the anatomy of the body and reclassified in accordance with the result;

wherein gaps between the cavity areas are closed by dilation and the area is expanded by dilation.

\* \* \* \* \*